United States Patent [19]

Abthoff et al.

[11] Patent Number: 4,617,795
[45] Date of Patent: Oct. 21, 1986

[54] EXHAUST GAS PIPE FOR INTERNAL-COMBUSTION ENGINES HAVING A RECEIVING OPENING FOR A HEATED PROBE FOR DETERMINING THE OXYGEN CONTENT OF THE EXHAUST GASES

[75] Inventors: Jörg Abthoff, Pluederhausen; Hans-Dieter Schuster, Schorndorf; Gunter Loose, Remseck; Günther Ebinger, Heiningen, all of Fed. Rep. of Germany

[73] Assignee: Daimler-Benz Aktiengesellschaft, Stuttgart, Fed. Rep. of Germany

[21] Appl. No.: 711,253

[22] Filed: Mar. 13, 1985

[30] Foreign Application Priority Data

Mar. 13, 1984 [DE] Fed. Rep. of Germany ....... 3409045

[51] Int. Cl.⁴ .............................................. G01N 27/26
[52] U.S. Cl. ..................................... 60/276; 204/410; 204/421; 204/424
[58] Field of Search ................. 60/276; 204/410, 421, 204/424, 425

[56] References Cited

U.S. PATENT DOCUMENTS

| | | | |
|---|---|---|---|
| 4,132,616 | 1/1979 | Tantram | 204/400 |
| 4,158,166 | 6/1979 | Isenberg | 204/426 |
| 4,208,266 | 6/1980 | Auman | 204/410 |
| 4,484,440 | 11/1984 | Oki | 60/323 |
| 4,571,285 | 2/1986 | Nakazawa | 204/425 |

FOREIGN PATENT DOCUMENTS 2233299 7/1972 Fed. Rep. of Germany .

*Primary Examiner*—Douglas Hart
*Attorney, Agent, or Firm*—Barnes & Thornburg

[57] ABSTRACT

A system is provided for measuring the amount of oxygen in exhaust gas emitted by an internal-combustion engine. The system includes an exhaust pipe for conducting engine exhaust gas and a probe for determining the oxygen content of engine exhaust gases. The exhaust pipe has a side wall formed to include an aperture for continuously discharging a portion of the engine exhaust gas flowing through the pipe. The system further includes a support housing for positioning the probe at a location outside of the exhaust pipe in proximity to the side wall aperture so that the probe is exposed to the engine exhaust gas portion discharged through the aperture and for collecting exhaust gas in a space surrounding the probe. The aperture is sized to permit exhaust gas collected in the support housing to be reintroduced into the exhaust pipe so that collected exhaust gas will be exchanged continuously with exhaust gas flowing through the exhaust pipe.

7 Claims, 1 Drawing Figure

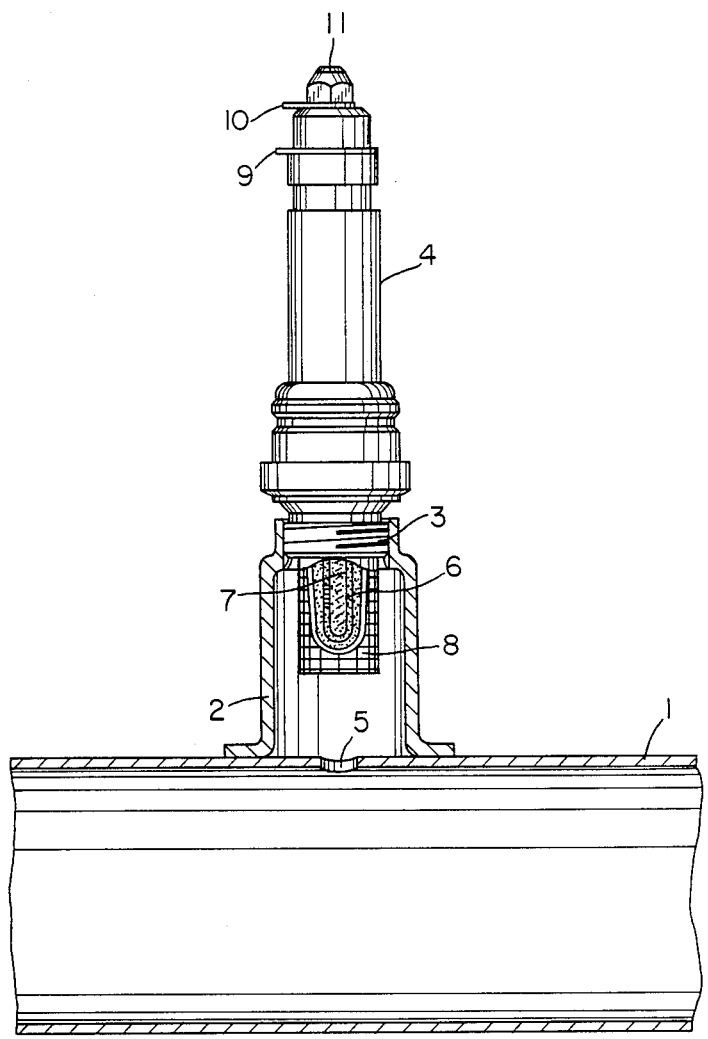

EXHAUST GAS PIPE FOR INTERNAL-COMBUSTION ENGINES HAVING A RECEIVING OPENING FOR A HEATED PROBE FOR DETERMINING THE OXYGEN CONTENT OF THE EXHAUST GASES

BACKGROUND AND SUMMARY OF THE INVENTION

This invention relates to an exhaust system for a motor vehicle, and particularly to a system for measuring the amount of oxygen in exhaust gas emitted by an internal-combustion engine.

In order to comply with exhaust gas regulations, it may be necessary to determine tne residual oxygen content in the exhaust gas of internal-combustion engines and, by using this value, regulate the fuel/air ratio on the intake side. Probes are generally used to determine the oxygen content in the exhaust gas that work according to the principle of an oxygen concentration chain. They normally consist of a pipe consisting of a solid electrolyte, sucn as $ZrO_2$ which is acted upon by the exhaust gas on one side and by a gas with a known oxygen content on the other side.

Heretofore, since tne solid electrolyte requires a working temperature of about 400° to 800° C., the probe had been screwed into the exhaust gas pipe through a receiving opening at a point where tne exnaust gases have the corresponding temperature in order to heat tne probe to its working temperature. However, it was found that the exhaust gas temperature also fluctuates considerably because of the considerably changing loads affecting the engine so that the danger exists that tne probe may either be overheated at full load or cooled during part load or coasting operations, and it may thus lose its effectiveness. It has therefore been tried to heat probes in order to make their working temperature more uniform. Although a better result is obtained by means of these heated probes, the danger still exists that the probe will be overheated during full-load operation or overcooled during coasting operation of the engine due to the design of the heating means unless the temperature of the probe is adapted to different exhaust gas temperatures by means of a very fast reacting and therefore extremely costly temperature control system.

One object of the present invention is therefore to find an exhaust gas pipe for internal-combustion engines having a receiving opening for a heated probe for determining the oxygen content of tne exhaust gases where an overheating or overcooling of the probe is reliably avoided without need for a costly temperature control system.

According to the present invention, a system is provided for measuring the amount of oxygen in exhaust gas emitted by an internal-combustion engine. The system includes an exhaust pipe for conducting engine exhaust gas and probe means for determining tne oxygen content of engine exhaust gases. The exhaust pipe has a side wall formed to include an aperture for continuously conducting a portion of the engine exhaust gas conducted through the pipe. The system further includes support means for positioning the probe means at a location outside of the exhaust pipe in proximity to the side wall aperture so that the probe means is exposed to the engine exhaust gas portion discharged through the aperture and for collecting exhaust gas in a space surrounding the probe means. The aperture is sized to permit exhaust gas collected in the support means to be reintroduced into the exhaust pipe so that collected exhaust gas will be exchanged continuously with exhaust gas flowing through tne exhaust pipe.

Preferred embodiments of the present invention provide an exhaust gas pipe with a recess or a blind hole, the side walls of which are located outside the exhaust gas flow. The overheated probe is mounted in this recess. The opening of the recess in the direction of the exhaust gas flow is smaller than the cross-section of the recess, cross-sections of from 1 to 200 mm² having been especially suitable. When tne cross-section of the opening becomes smaller than 1 mm², there will no longer be a sufficient gas exchange with the exhaust gas flowing in the exhaust gas pipe, and the determination of the composition of the exhaust gas will take place too slowly. When the opening of the recess or the blind hole in the direction of the exhaust gas flow is larger than 200 mm², the gas exchange with the exhaust gas flowing in the exhaust gas pipe is so brisk that overheating as well as overcooling of the probe may occur. Cross-sections of from 3 to 50 mm² for the opening of the recess are preferred. In the case of these small cross-sections, a sufficient exchange with the gas filling located in the recess will still take place because of the pulsations of the exhaust gas in the exhaust gas pipe.

In addition, the depth of the recess must be dimensioned in such a way that the point of the probe is set back with respect to the opening to the exhaust gas flow in order to protect it from the attack by particles located in the exhaust gas and which enter the recess through the recess opening. A setback between the point of the probe and the recess opening also contributes to making the probe temperature more uniform. Good results are obtained when the depth of tne recess is dimensioned in such a way that the point of the probe is set back with respect to the opening to the exhaust gas flow by approximately 5 to 90 mm. A useful rule is that the depth of the recess should be the larger, or the point of the probe should be the further set back with respect to the opening to the exhaust gas flow, the larger the opening is in the direction of the exhaust gas.

It was also found to be advantageous for the clearance of the recess to be dimensioned in such a way that the distance of the wall of the recess to the wall of the probe is about 1 to 10 mm. In the case of such a design of the recess, the gas volume located in the recess is relatively small so that the probe works without much delay caused by a gas volume to be changed that is too large. The wall of the probe in this case is the actual wall of the probe, i.e., the solid-electrolyte pipe, in which case protective devices that may be arranged around the solid-electrolyte pipe, such as a sheet-metal covering or a wire basket, for preventing unintended contact with the sensitive ceramics of the solid electrolyte, are not taken into account with respect to the dimensioning.

The manufacturing of the exhaust gas pipe may, for example, take place by providing the exhaust gas pipe with a bore which represents the opening of the recess to the exhaust gas flow and by welding or soldering a hat-shaped recess or blind hole provided with a thread for receiving the probe at this point onto the exhaust gas pipe. In addition, the recess may be provided witn a thermic insulation.

Further objects, features, and advantages of the present invention will become more apparent from the following description when taken with he accompanying drawings which show, for purposes of illustration only, an embodiment in accordance with the present invention.

BRIEF DESCRIPTION OF THE DRAWING

The drawing shows a preferred embodiment of the present inventory with portions broken away.

DETAILED DESCRIPTION OF THE DRAWING

The drawing shows an exhaust gas pipe with a partial section of a heated probe. A hat-shaped recess 2 which, at its upper end, has a thread 3 for receiving the probe 4 is welded onto the exhaust gas pipe 1. The inside of the recess is connected with the exhaust gas flow via the opening 5. The probe 4, a known construction, is shown only as a partial section. The solid electrolyte 6 can be recognized which is provided on both sides witn a metal layer for the removal of the electromotive force (emf) as well as a heating spiral 7 for the heating. A protecting basket 8 is arranged around tne solid electrolyte and has the purpose of preventing accidental contamination by touching, etc., during the mounting or handling of the probe. The heating spiral 7 is supplied with energy via the supply points 9 and 10, while the probe emf is removed via the contact 11 and the vehicle mass (exhaust pipe). The necessary insulating materials required for the separation of the different circuits are not shown in detail.

Although the invention has been described in detail with reference to certain preferred embodiments and specific examples, variations and modifications exist within the scope and spirit of the invention as described and defined in the following claims.

What is claimed is:

1. A system for measuring the amount of oxygen in exhaust gas emitted by an internal combustion engine and flowing through an exhaust pipe, the system comprising:

sidewall aperture means in said exhaust pipe for accommodating a portion of exhaust gas to be monitored;

sensing probe housing means including housing wall means defining a probe accommodating chamber bounded by inner surfaces of said housing wall means, said sensing probe housing means being located entirely outside of said exhaust pipe such that only said inner surfaces of said housing wall means are impinged by any exhaust gas, said exhaust gas impinging on said inner surfaces being said portion of exhaust gas to be monitored, with outer surfaces of said sensor probe housing means being free of impingement by any exhaust gas; and probe means for determining the oxygen content of engine exhaust gases, with at least a portion of said probe means positioned in said probe accommodating chamber which senses the oxygen content in said portion of exhaust gas, said probe means being free of any impingement by any exhaust gas except by said portion to be monitored disposed in said probe accommodating chamber.

2. The system of claim 1, wherein the sidewall aperture is sized to permit exhaust gas to flow freely from the exhaust pipe into the probe accommodating chamber and vice versa so that monitored exhaust gas will be exchanged continuously with exhaust gas flowing through the exhaust pipe.

3. The system of claim 2, wherein the sidewall aperture has a cross-sectional area of between 1 and 200 $mm^2$.

4. The system of claim 1, wherein the sensing probe housing means is hat-shaped and has a threaded portion for receiving the probe means at one end and flange means for engaging a side wall of the exhaust pipe in sealing relation at the other end.

5. The system of claim 4, wherein the probe means includes a forward tip, and the forward tip is set back a distance of between 5 and 90 mm in relation to the sidewall aperture when the probe means is received in its mounted position within the hat-shaped sensor probe housing means.

6. The system of claim 4, wherein the probe means has an exterior side wall, and the probe means is positioned within the probe accommodating chamber to define a clearance distance between the inner surfaces of said housing wall means defining the probe accommodating chamber and the exterior side wall of the probe means of between 1 and 10 mm.

7. The system of claim 1, wherein the probe means is a solid electrolyte.

* * * * *